United States Patent
Goda

(10) Patent No.: US 9,516,878 B2
(45) Date of Patent: *Dec. 13, 2016

(54) AQUEOUS CHLOROUS ACID SOLUTION FOR USE AS DISINFECTANT

(71) Applicant: Honbu Sankei Co., Ltd., Osaka (JP)

(72) Inventor: Hisataka Goda, Osaka (JP)

(73) Assignee: Honbu Sankei Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/563,564

(22) Filed: Dec. 8, 2014

(65) Prior Publication Data

US 2015/0093482 A1  Apr. 2, 2015

Related U.S. Application Data

(60) Division of application No. 13/862,879, filed on Apr. 15, 2013, now abandoned, which is a continuation of
(Continued)

(30) Foreign Application Priority Data

Aug. 28, 2006  (JP) ................. 2006-231280

(51) Int. Cl.
*A01N 59/08*  (2006.01)
*C01B 11/08*  (2006.01)
(Continued)

(52) U.S. Cl.
CPC .............. *A01N 25/22* (2013.01); *A01N 59/00* (2013.01); *A01N 59/14* (2013.01); *A01N 59/26* (2013.01);
(Continued)

(58) Field of Classification Search
CPC .......... A23L 3/358; A23L 3/3508; A23L 3/34; A23L 3/3454; A01N 59/00; A01N 25/22; C01B 11/08
See application file for complete search history.

(56) References Cited

U.S. PATENT DOCUMENTS

| 4,891,216 A | 1/1990 | Kross et al. |
| 4,902,498 A | 2/1990 | Agricola et al. |
| (Continued) | | |

FOREIGN PATENT DOCUMENTS

| CA | 1339066 | 7/1997 |
| CN | 1279584 A | 1/2001 |
| (Continued) | | |

OTHER PUBLICATIONS

Office Action for corresponding Australian Patent Application No. 2013205834 dated Sep. 26, 2014.
(Continued)

*Primary Examiner* — Lakshmi Channavajjala
(74) *Attorney, Agent, or Firm* — Renner, Otto, Boisselle & Sklar, LLP

(57) ABSTRACT

A process for producing aqueous chlorous acid solution in which chlorous acid, which is safe for the human body, is easy to handle, and less generates chlorine dioxide, is yielded and used as a disinfectant for a pretreatment in food processing. To an aqueous sodium chlorate solution is added sulfuric acid or an aqueous solution thereof in such an amount and concentration that the pH of the aqueous solution can be kept at 2.3-3.4 to thereby react them and generate chloric acid. Subsequently, hydrogen peroxide is added to the chloric acid in an amount which is equal to or larger than the amount necessary for a reduction reaction to thereby yield chlorous acid. Any one of inorganic acids, inorganic acid salts, organic acids, and organic acid salts, or two or more thereof, or a combination or these is added to the aqueous solution containing chlorous acid yielded, whereby the chlorous and acid can be present for long and the pH of
(Continued)

the aqueous solution is regulated to regulated to 3.2-7.0. Thus, high bactericidal power is imparted thereto.

13 Claims, 9 Drawing Sheets

Related U.S. Application Data application No. 12/439,226, filed as application No. PCT/JP2007/066691 on Aug. 28, 2007, now Pat. No. 8,951,576.

(51) Int. Cl.
    *A23L 3/358*      (2006.01)
    *A01N 25/22*      (2006.01)
    *A01N 59/00*      (2006.01)
    *A01N 59/14*      (2006.01)
    *A01N 59/26*      (2006.01)
    *A23L 3/3508*      (2006.01)

(52) U.S. Cl.
    CPC ............ *A23L 3/3508* (2013.01); *A23L 3/358* (2013.01); *C01B 11/08* (2013.01); *A23V 2002/00* (2013.01)

(56) References Cited

U.S. PATENT DOCUMENTS

| | | | |
|---|---|---|---|
| 5,366,714 | A | 11/1994 | Bigauskas |
| 5,389,390 | A | 2/1995 | Kross |
| 6,063,425 | A | 5/2000 | Kross et al. |
| 6,524,624 | B1 | 2/2003 | Morelli et al. |
| 7,824,556 | B2 | 11/2010 | Sampson et al. |
| 2001/0001655 | A1 | 5/2001 | Kuke |
| 2004/0175322 | A1 | 9/2004 | Woodruff et al. |
| 2005/0008554 | A1 | 1/2005 | Nowosielski-Slepowron et al. |
| 2006/0039841 | A1 | 2/2006 | Rico et al. |

FOREIGN PATENT DOCUMENTS

| | | |
|---|---|---|
| EP | 0287074 | 10/1988 |
| EP | 0482811 | 4/1992 |
| EP | 0565134 A1 | 10/1993 |
| JP | 11-503995 | 4/1999 |
| JP | 2003-515309 A | 5/2003 |
| JP | 2004-175686 | 6/2004 |
| JP | 2004-337582 | 12/2004 |
| WO | WO 99/18805 | 4/1999 |

OTHER PUBLICATIONS

Office Action for corresponding Chinese Patent Application No. 201310226566.1 dated May 6, 2014 and its English translation.
Office Action for corresponding Japanese Patent Application No. 2013-018424 dated Jun. 11, 2014 and partial English translation.
Allowed claims of co-pending related U.S. Appl. No. 12/439,226, filed Aug. 30, 2010.
Invitation Pursuant to Article 94(3) and Rule 71(1) EPC for corresponding European Patent Application No. 07 806 168.6 dated Mar. 17, 2015.
Office Action for corresponding Japanese Patent Application No. 2013-018424 dated Feb. 5, 2015 and its partial English translation.
Office Action for corresponding Chinese Patent Application No. 201310226566.1 dated Dec. 5, 2014 and its partial English translation.
Official Action for corresponding Chinese Application No. 201310226566.1 issued on Sep. 1, 2015 and its partial English translation.
Examination Report for corresponding Australian Application No. 2015201401 issued on Dec. 18, 2015.
Extended European Search Report for corresponding European Application No. 15002624.3 dated Jan. 20, 2016.
Official Action for corresponding Chinese Application No. 201310226566.1 issued on May 9, 2016 and its partial English translation.
Patent Examination Report for corresponding Australian Application No. 2015203851 issued on Sep. 7, 2016.

AQUEOUS CHLOROUS ACID SOLUTION FOR USE AS DISINFECTANT

TECHNICAL FIELD

The present invention relates to a process for producing an aqueous chlorous acid solution used for disinfection/sterilization of food for pretreatment in food processing operations and related facilities.

BACKGROUND ART

Conventionally, chlorine oxides (e.g., chlorine, hypochlorous acid, chlorous acid, and chlorine dioxide) are primarily used for disinfection or sterilization of food for pretreatment in food processing operations, such as fresh perishable food including vegetables and fruits, and the facilities related to processing and production of processed food, such as containers, preparation/cooking machinery, and plant equipment. Of these, chlorine and hypochlorous acid, when reacted with organic compounds, are known to produce trihalomethanes, which are carcinogenic compounds. This, along with recent health-consciousness trend, has focused attention on acidified sodium chlorite (ASC) solution, which was developed in the United States of America and which possesses a high bactericidal effect and is less associated with trihalomethane-related adverse effects. Reference 1: U.S. Pat. No. 6,524,624

To produce the above-mentioned ASC solution, an aqueous chlorous acid solution is mixed with an acid known as "generally recognized as safe" (GRAS) and adjusted to pH 2.3 to 3.2.

However, the main active component of the above-mentioned ASC solution, chlorous acid, decomposes a short time after preparation due to its low stability, thereby reducing its bactericidal potential. The above-mentioned ASC solution, therefore, needs to be prepared immediately before use.

This preparation procedure is not only inconvenient but also associated with the disadvantages resulting from production of chlorine dioxide gas, which is highly likely to have toxic effects on individuals who inhale it and corrosive effects on food-processing and cooking machinery and other related equipment.

DISCLOSURE OF INVENTION

Problem to be Solved by Invention

The present invention was made taking into account the above disadvantages. The purpose of the present invention is to provide an easy-to-handle, long-acting, stable aqueous chlorous acid solution. Another purpose of the present invention is to provide a disinfectant for use in pretreatment of food-processing operations that releases a reduced amount of chlorine dioxide, is safe to human health, and possesses a high bactericidal activity.

Means for Solving Problems

In order to solve the aforementioned problems, a first feature of the process of the present invention is to employ a process for producing an aqueous chlorous acid solution for use as disinfectant, comprising: reacting an aqueous sodium chlorate solution with a volume and concentration of sulfuric acid or aqueous solution thereof appropriate for maintaining pH of said aqueous solution at 2.3 to 3.4, thereby generating chloric acid, and subsequently adding thereto at least an amount of hydrogen peroxide required for reducing said chloric acid to produce chlorous acid.

A second feature of the process of the present invention is to employ a process for producing an aqueous chlorous acid solution for use as disinfectant, comprising: reacting an aqueous sodium chlorate solution with a volume and concentration of sulfuric acid or aqueous solution thereof appropriate for maintaining pH of said aqueous solution at 2.3 to 3.4, thereby generating chloric acid, subsequently adding thereto at least an amount of hydrogen peroxide required for reducing said chloric acid to produce chlorous acid, and adding to the resulting aqueous solution at least one compound selected from the group consisting of inorganic acids and salts or a combination thereof, to adjust its pH in the range of 3.2 to 7.0.

A third feature of the process of the present invention is to employ a process for producing an aqueous chlorous acid solution for use as disinfectant, comprising: reacting an aqueous sodium chlorate solution with a volume and concentration of sulfuric acid or aqueous solution thereof appropriate for maintaining pH of said aqueous solution at 2.3 to 3.4, thereby generating chloric acid, subsequently adding thereto at least an amount of hydrogen peroxide required for reducing said chloric acid to produce chlorous acid, and adding to the resulting aqueous solution at least one compound selected from the group consisting of inorganic and organic acids and salts or a combination thereof, to adjust its pH in the range of 3.2 to 7.0.

A forth feature of the process of the present invention is to employ a process for producing an aqueous chlorous acid solution for use as disinfectant, comprising: reacting an aqueous sodium chlorate solution with a volume and concentration of sulfuric acid or aqueous solution thereof appropriate for maintaining pH of said aqueous solution at 2.3 to 3.4, thereby generating chloric acid, subsequently adding thereto at least an amount of hydrogen peroxide required for reducing said chloric acid to produce chlorous acid, adding to the resulting aqueous solution at least one compound selected from the group consisting of inorganic acids and salts or a combination thereof, and further adding at least one compound selected from the group consisting of inorganic and organic acids and salts or a combination thereof, to adjust the pH in the range of 3.2 to 7.0.

A fifth feature of the process of the present invention is to employ the process for producing an aqueous chlorous acid solution for use as disinfectant, wherein said inorganic acid according to any of second to forth features of the present process, include carbonic acid, phosphoric acid, boric acid, or sulfuric acid.

A sixth feature of the process of the present invention is to employ the process for producing an aqueous chlorous acid solution for use as disinfectant, wherein said inorganic salts according to any of second to fifth features of the present process include carbonates, hydroxides, phosphates, or borates.

A seventh feature of the process of the present invention is to employ the process for the process for producing an aqueous chlorous acid solution for use as disinfectant, wherein said carbonates according to the sixth feature of the present process include sodium carbonate, potassium carbonate, sodium bicarbonate, or potassium bicarbonate.

A eighth feature of the process of the present invention is to employ the process for the process for producing an aqueous chlorous acid solution for use as disinfectant, wherein said hydroxides according to the sixth or the seventh feature include sodium hydroxide or potassium hydroxide.

A ninth feature of the process of the present invention is to employ the process for producing an aqueous chlorous acid solution for use as disinfectant, wherein said phosphates according to any one of sixth to eight features include disodium hydrogenphosphate, sodium dihydrogenphosphate, trisodium phosphate, tripotassium phosphate, dipotassium hydrogenphosphate, or potassium dihydrogenphosphate.

A tenth feature of the process of the present invention is to employ the process for producing an aqueous chlorous acid solution for use as disinfectant, wherein said borates according to any one of sixth to ninth features include sodium borate or potassium borate.

A eleventh feature of the process of the present invention is to employ the process for producing an aqueous chlorous acid solution for use as disinfectant, wherein said organic acids according to any one of third to tenth features include succinic acid, citric acid, malic acid, acetic acid, or lactic acid.

A twelfth feature of the process of the present invention is to employ the process for producing an aqueous chlorous acid solution for use as disinfectant, wherein said organic salts according to any one of third to eleventh features include sodium succinate, potassium succinate, sodium citrate, potassium citrate, sodium malate, potassium malate, sodium acetate, potassium acetate, sodium lactate, potassium lactate, or calcium lactate Advantagious Effect of the Invention According to the present invention, there can be provided an aqueous chlorous acid solution which is highly disinfectant and stable, so that it will not need to be prepared immediately before being used and it is made possible to be preserved for future use. In addition, it prevents generation of chlorine dioxide so as to be harmless to human body and can be used without anxiety.

Moreover, the aqueous chlorous acid solution produced in accordance with the present invention can maintain prolonged stability and can be marketed as disinfectant commodities.

BEST MODE FOR CARRING OUT THE INVENTION

Figure 1:
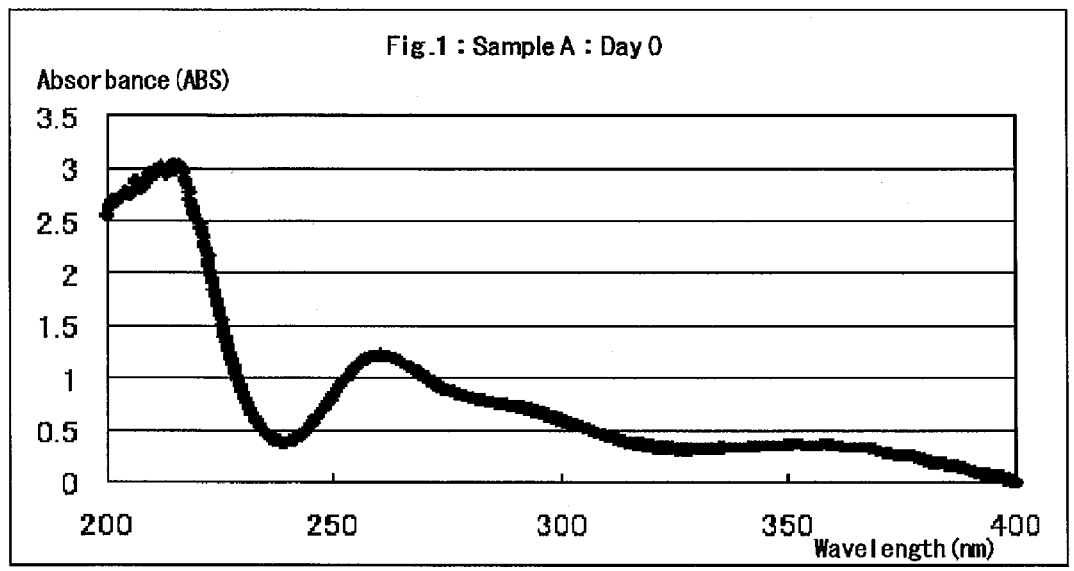
FIG. 1 shows the results of spectrophotometric measurement of sample A conducted on the day of preparation.
Figure 2:
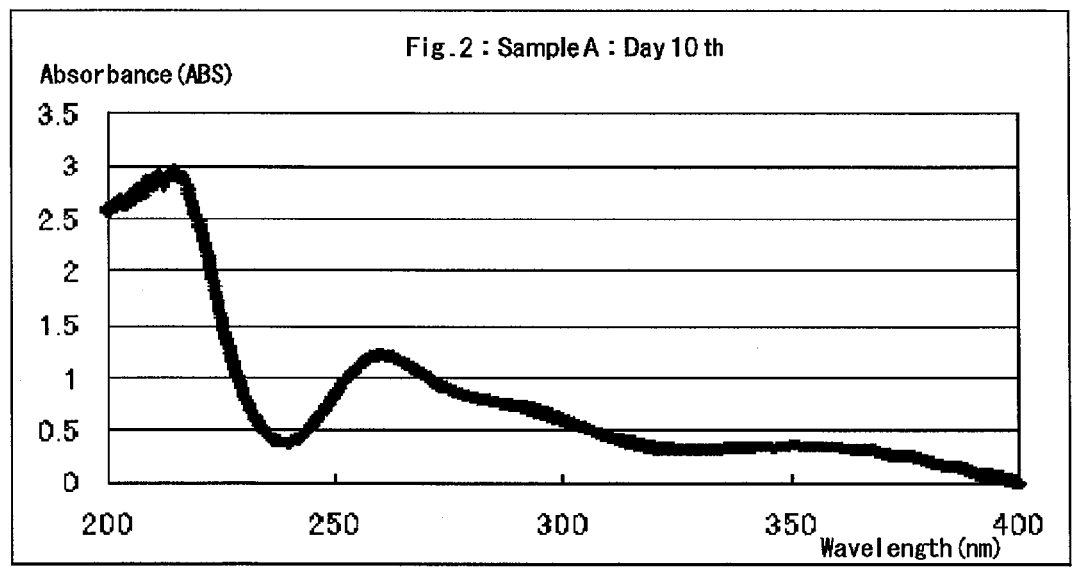
FIG. 2 shows the results of spectrophotometric measurement of sample A conducted on day 10 of preparation.
Figure 3:
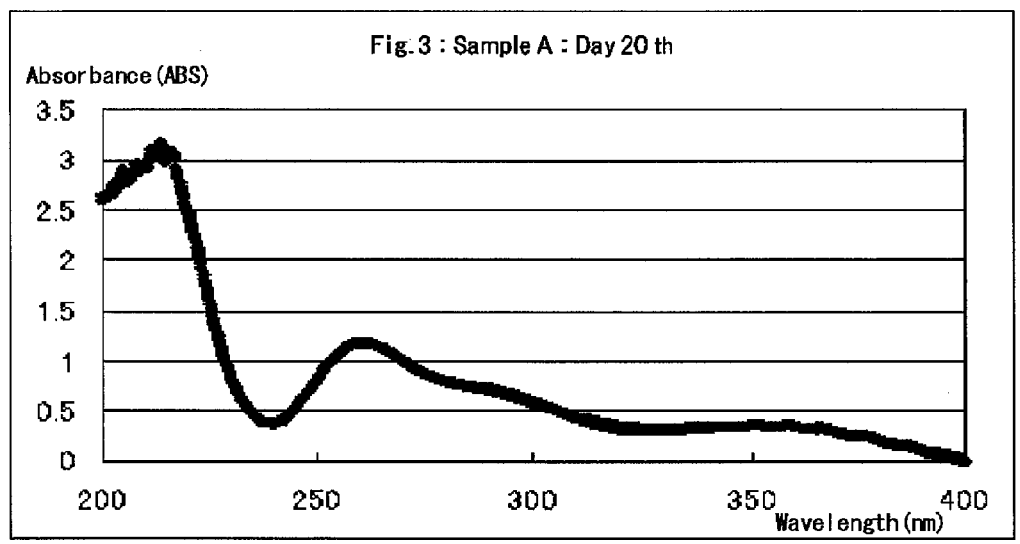
FIG. 3 shows the results of spectrophotometric measurement of sample A conducted on day 20 of preparation.

Hereinafter, the preferred embodiments of the present invention will be described with reference to accompanying figures and tables.

Example 1

Example 1 of the present invention provides a process for producing an aqueous chlorous acid ($HClO_2$) solution for use as disinfectant. According to this process, sulfuric acid ($H_2SO_4$) or aqueous solution thereof is added to an aqueous sodium chlorate ($NaClO_3$) solution to create acidic conditions, thereby generating chloric acid ($HClO_3$), and the resulting chloric acid undergoes a reduction reaction with an excess amount of hydrogen peroxide to produce chlorous acid ($HClO_2$). The essential chemical reactions of this production process are presented by the following equations A and B:

Chemical Formula 1

$$2NaClO_3 + H_2SO_4 \rightarrow 2HClO_3 + Na_2SO_4\downarrow \qquad \text{(Equation A)}$$

$$HClO_3 + H_2O_2 \rightarrow HClO_2 + H_2O + O_2\uparrow \qquad \text{(Equation B)}$$

Equation A indicates that chloric acid is generated by addition of an amount and concentration of sulfuric acid ($H_2SO_4$) or aqueous solution thereof appropriate for maintaining the pH of the aqueous sodium chlorate ($NaClO_3$) solution at 2.3 to 3.4, while sodium ions are eliminated concurrently.

Then, equation B shows that chloric acid ($HClO_3$) undergoes a reduction reaction with hydrogen peroxide ($H_2O_2$) to produce chlorous acid ($HClO_2$). This reaction requires the addition of at least an amount of hydrogen peroxide (or aqueous solution thereof) stoichiometrically required for the reduction reaction. Otherwise, the reaction will yield only chlorine dioxide.

Chemical Formula 2

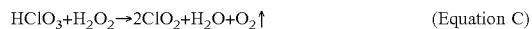

$$HClO_3 + H_2O_2 \rightarrow 2ClO_2 + H_2O + O_2\uparrow \qquad \text{(Equation C)}$$

$$2ClO_2 + H_2O_2 \rightarrow 2HClO_2 + O_2\uparrow \qquad \text{(Equation D)}$$

$$2ClO_2 + H_2O \leftrightarrow HClO_2 + HClO_3 \qquad \text{(Equation E)}$$

$$2HClO_2 \leftrightarrow H_2O + Cl_2O_3 \qquad \text{(Equation F)}$$

In cases where chlorine dioxide is generated, it will be converted to chlorous acid by a series of reactions shown by equations C to F.

Chlorous acid ($HClO_2$) thus produced possesses the propensity to decompose quickly to chlorine dioxide gas or chlorine gas by interactions among a plurality of chlorous acid molecules or by the presence of chloride (Cl⁻) ions, hypochlorous acid (HClO), or other reductive agents. It is, therefore, necessary to provide a long-acting chlorous acid ($HClO_2$) preparation effective for use as disinfectant.

Under these circumstances, it is necessary to provide a process for producing a stable, long-acting aqueous chlorous acid ($HClO_2$) solution; and this is achieved by creating a transitional state to delay the progress of the decomposition reaction through the addition of at least one compound selected from the group consisting of inorganic and organic acids and salts or a combination thereof, to the aqueous chlorous acid ($HClO_2$) solution produced according to the process described in Example 1 above. This process is embodied in Examples 2, 3, and 4.

Example 2

Specifically, according to Example 2, the aqueous chlorous acid (HON solution produced according to the process described in Example 1 is mixed with inorganic acid(s) or organic salt(s), or more specifically, at least one compound selected from the group consisting of carbonates and hydroxides or a combination thereof.

Example 3

Also, according to Example 3, the aqueous solution produced in Example 2 is mixed with at least one compound selected from the group consisting of inorganic and organic acids and salts or a combination thereof.

Example 4

Moreover, according to Example 4, the aqueous solution produced in Example 1 is mixed with at least one compound selected from the group consisting of inorganic and organic acids and salts or a combination thereof.

As for the above, inorganic acids can be mentioned as well as carbonic acid, phosphoric acid, boric acid, and sulfuric acid. For the inorganic salts, carbonates and hydroxides can be mentioned as well as phosphates and borates. More specifically, the carbonates include sodium carbonate, potassium carbonate, sodium bicarbonate, and potassium bicarbonate; the hydroxides include sodium hydroxide and potassium hydroxide; the phosphates include disodium hydrogenphosphate, sodium dihydrogenphosphate, trisodium phosphate, tripotassium phosphate, dipotassium hydrogenphosphate, and potassium dihydrogenphosphate; and the borates include sodium borate and potassium borate. Moreover, the above organic acids include succinic acid, citric acid, malic acid, acetic acid, and lactic acid; and appropriate examples of the organic salts include sodium succinate, potassium succinate, sodium citrate, potassium citrate, sodium malate, potassium malate, sodium acetate, potassium acetate, sodium lactate, potassium lactate, and calcium lactate.

In Examples 2, 3, and 4, the following transitional states are temporarily created:

$$Na^+ + ClO_2^- \rightleftarrows Na\text{---}ClO_2,$$

$$K^+ + ClO_2^- \rightleftarrows K\text{---}ClO_2,$$

$$H^+ + ClO_2^- \rightleftarrows H\text{---}ClO_2.$$

These states contribute to delaying the progress of the conversion of chlorous acid ($HCl_2$) to chlorine dioxide ($ClO_2$), which enables the formation of an aqueous chlorous acid solution that is capable of sustaining chlorous acid ($HClO_2$) for an extended time and releases a reduced amount of chlorine dioxide ($ClO_2$).

Now, the lower the pH value (the stronger the acidity) of a chlorine oxide, the stronger its bactericidal potential is known to be. The tables below show the results of experiments on the relationship between pH values and bactericidal powers. In these experiments, a pathogenic Escherichia coli strain (O157:H7) was used as the test microbe. Sodium chlorite (Wako Pure Chemical Industries, Ltd., Osaka, Japan, 80%) was used as the test chlorine oxide. Citric acid (Wako, 98%), lactic acid (Wako, 85% to 92%), and acetic acid (Wako, 99.7%) were used as an activator. Thirty-mL aliquots of an aqueous sodium chlorite solution (0.5 g/L, pH 9.8) were adjusted to pH 2.0, 3.0, 4.0, 5.0, 6.0, 7.0, and 8.0 by addition of citric acid, lactic acid, or acetic acid. Phenol index measurement procedure was employed for assessment of the bactericidal effect. Ten-mL aliquots of the test solutions diluted as appropriate were transferred to test tubes, allowed to warm for at least 5 minutes in a thermostatic water bath set at 20° C.±1° C. Then, 1-mL aliquots of the test microbe preparation, pre-warmed in a similar manner, were added to the test tubes, and sampling was performed by use of a platinum loop at 2.5, 5, 10, and 15 minutes after the addition. The sampled microbial mixtures were inoculated into a normal bouillon medium and incubated at 37° C. for 48 hours. Bacterial growth was visually observed; positive growth was designated as '+' and negative growth as '−.'

TABLE 1

Bactericidal potential for sodium chlorite solution: Activator Citric acid

| time (min.) | pH | | | | | |
|---|---|---|---|---|---|---|
| | 3.0 | 4.0 | 5.0 | 6.0 | 7.0 | 8.0 |
| 2.5 | − | − | + | + | + | + |
| 5 | − | − | + | + | + | + |
| 10 | − | − | − | + | + | + |
| 15 | − | − | − | − | + | + |

TABLE 2

Bactericidal potential for sodium chlorite solution: Activator Lactic acid

| time (min.) | pH | | | | | |
|---|---|---|---|---|---|---|
| | 3.0 | 4.0 | 5.0 | 6.0 | 7.0 | 8.0 |
| 2.5 | − | − | + | + | + | + |
| 5 | − | − | + | + | + | + |
| 10 | − | − | − | + | + | + |
| 15 | − | − | − | − | + | + |

TABLE 3

Bactericidal potential for sodium chlorite solution: Activator Acetic acid

| time (min.) | pH | | | | | |
|---|---|---|---|---|---|---|
| | 3.0 | 4.0 | 5.0 | 6.0 | 7.0 | 8.0 |
| 2.5 | − | − | + | + | + | + |
| 5 | − | − | + | + | + | + |
| 10 | − | − | − | + | + | + |
| 15 | − | − | − | − | + | + |

As shown in the tables above, aqueous sodium chlorite solutions having pH 7.0 or higher fell short of completely eradicating the test E. coli strain in 15 minutes. However, complete eradication was achieved in 2.5 minutes when the pH was adjusted to 4.0 or lower, in 10 minutes when the pH was adjusted to 5.0, and in 15 minutes when the pH was adjusted to 6.0. These findings demonstrate a higher bactericidal potential for sodium chlorite solution having a more acidic pH value. These findings also demonstrate that the difference in the type of activator poses no significant difference in the bactericidal power of sodium chlorite solution.

Thus, chlorite solution exhibits a stronger bactericidal effect when it is more acidic. However, when its pH is strongly acidic, for example, at a value in the order of 2.0, its applicable areas in food industry are limited because of its negative effects such as denaturation of protein components of the sterilized food items.

Chemical Formula 3

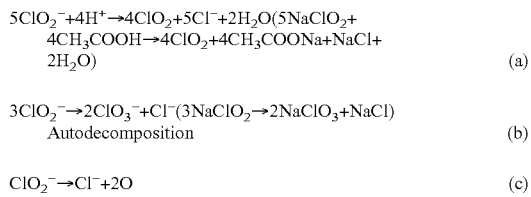

The above Chemical Formula 3 represents the decomposition of chlorite compounds in an acidic solution. When the solution has a lower (more acidic) pH value, the decomposition of chlorite compounds is enhanced, that is, the absolute kinetic rates of the reactions represented by above equations (a), (b), and (c) become elevated. Practically, with a decreased pH value, the dominance of the reaction products of equation (a) is reduced. However, with a decrease in pH, the total decomposition percentage shifts to a larger value, resulting in an increased amount of $ClO_2$ (chlorine dioxide) generated. Therefore, the lower the pH value of the aqueous solution becomes, the more likely it makes the disinfectant harmful to human health and disinfection operation awkward due to the release of toxic and irritating $ClO_2$ gas, although it improves the bactericidal and bleaching potentials. Also, a lower pH solution renders chlorous acid more unstable, and thereby enhances the conversion of chlorous acid to chlorine dioxide. As a result, the duration of the bactericidal activity is reduced.

Therefore, when an aqueous chlorous acid ($HClO_2$) solution is mixed with any of the above-mentioned inorganic acids, inorganic salts, organic acids, or organic salts, the solution should be adjusted to pH 3.2 to 7.0, from the viewpoint of suppressing chlorine dioxide release and maintaining the bactericidal activity. The pH values should reach as high as allowed by the requirements on the bactericidal activity conditions within the above range. This contributes to producing an aqueous chlorous acid solution emitting a reduced amount of chlorine dioxide ($ClO_2$) by slowing the conversion of chlorous acid to sodium chlorite ($NaClO_2$) while maintaining chlorous acid ($HClO_2$) for an extended time.

As described below, to confirm the effects of the present invention, the following samples were prepared and subjected to measurement.

First, a chlorous acid solution prepared according to Example 1 was mixed with 1 moUL sodium carbonate to pH 5.7. The solution (corresponding to an aqueous chlorous acid solution prepared according to Example 2) was added to a 0.05 moUL sodium borate/succinate buffer (pH 5.7) to give a 3% chlorous acid content. To sum up, this solution (corresponding to an aqueous chlorous acid solution prepared according to Example 3) was prepared by adding to an aqueous chlorous acid solution an inorganic salt compound, followed by addition of a combination of an inorganic salt and an organic salt as buffer. This solution was termed sample A.

Second, the chlorous acid solution prepared according to Example 1 was mixed with 1 mol/L sodium carbonate to pH 5.7. Subsequently, this solution was mixed with deionized water to give a 3% chlorous acid content. In other words, this solution (corresponding to an aqueous chlorous acid solution prepared according to Example 2) was prepared by adding to an aqueous chlorous acid solution an inorganic salt compound. This solution was termed sample B.

Moreover, an aqueous solution containing 25.0% chlorous acid (Wako, 80%) was mixed with 1 mol/L solution of citric acid (Wako, 98%) to pH 2.6. The resulting solution was mixed with deionized water to give a 3% chlorous acid content. This process corresponds to a conventional technique for preparing above-mentioned ASC solution. This solution was termed sample C.

Furthermore, the chlorous acid solution prepared according to Example 1 was added to 0.05 mol/L sodium borate/succinate buffer (pH 6.8) to give a final pH of 5.7 and a chlorous acid content of 3%. In other words, this solution (corresponding to an aqueous chlorous acid solution prepared according to Example 4) was prepared by adding to an aqueous chlorous acid solution a combination of an inorganic salt and an organic salt as buffer. This solution was termed sample D.

The time-course stability of chlorous acid ($HClO_2$) in each sample was compared by measurement of UV spectra and molecular content. The measurement samples all contained 3% chlorous acid ($HClO_2$). UV spectrum measurement was conducted on a spectrophotometer adjusted to provide an absorbance of approximately 1 at the wavelength of maximum absorption when used to measure sample solutions diluted with an appropriate volume of ion exchanged water. Measurement of chlorous acid content was performed by the iodometric titration method described hereafter. Samples were aerated in an airtight container to eliminate chlorine dioxide dissolved in the samples. Then, approximately 10 g of each sample was measured accurately, and water was added to make the volume precisely 100 mL. These solutions were designated as test solutions. A volume of each of the test solutions containing approximately 0.06 g of chlorous acid ($HClO_2$) was accurately measured, placed in an iodine flask, mixed with 12 mL of sulfuric acid (3→100), and water was added to make the volume approximately 55 mL. Immediately after adding 4 g of potassium iodide to the solution, the flask was stoppered and kept in a dark place for 15 minutes. Titration was performed by using 0.1 mol/L sodium thiosulfate and a starch indicator, and the amount of chlorous acid in the solution was determined by the formula: 1 mL of 0.1 mol/L sodium thiosulfate solution=0.001711 g of $HClO_2$. Separately, blank tests were conducted for correction. The test solutions were stored in a dark place for preservation tests. Aliquots of the test solutions were subjected to measurements of chlorous acid content, UV absorption, and pH values immediately after preparation and at 1, 2, 3, 24, 48, 72, 96, 120, 240, 480, and 720 hours after preparation.

Consequently, the spectrometric measurement results identified two absorption peaks in the wavelength range of 248 to 420 nm immediately after preparation of samples A, B, C, and D: one absorption peak in the vicinity of 260 nm corresponding to acidic chlorite ions ($H^+ + ClO_2^-$) and the other absorption peak near 350 nm corresponding to chlorine dioxide ($ClO_2$). These results demonstrate the presence of chlorous acid ($HClO_2$) (FIGS. 1, 5, 9, and 13), because they indicate the concurrently ongoing chain of reactions shown in Chemical Formula 4 involving chlorous acid ($HClO_2$), chlorine dioxide ($ClO_2$), and acidic chlorite ion ($ClO_2$).

Table 4 depicts the changes over time in chlorous acid content. The results show that sample C (ASC) lost half of the initial chlorous acid content within 2 hours after preparation, and lost it almost completely on day 4. On the other hand, samples A, B, and D retained much of the initial chlorous acid content even on day 30. Therefore, the aqueous chlorous acid solutions of the present invention are superior to conventional disinfectants, because they maintain chlorous acid content for an extended time.

Of these, samples A and D maintained the initial chlorous acid content (prepared on day 0) for 30 days. This indicates that the aqueous chlorous acid solutions prepared according to Examples 3 and 4 possess the highest capacities of maintaining the stability of chlorous acid over time.

TABLE 4

Comparison of maintenance of chlorous acid ($HClO_2$) in solutions ($HClO_2$ content 3%)

| | \multicolumn{12}{c}{time course} |
|---|---|---|---|---|---|---|---|---|---|---|---|---|
| | 0 hr | 1 hr | 2 hr | 3 hr | 24 hr | 48 hr | 72 hr | 96 hr | 120 hr | 240 hr | 480 hr | 720 hr |
| Sample A | + | + | + | + | + | + | + | + | + | + | + | + |
| | 3.0 | 3.0 | 3.0 | 3.0 | 3.0 | 3.0 | 3.0 | 3.0 | 3.0 | 2.9 | 2.8 | 2.7 |
| Sample B | + | + | + | + | + | + | + | + | + | + | + | + |
| | 3.2 | 3.2 | 3.2 | 3.2 | 3.1 | 3.0 | 3.0 | 2.9 | 2.9 | 2.6 | 2.3 | 2.1 |
| Sample C | + | + | − | − | − | − | − | − | − | − | − | − |
| | 3.0 | 1.9 | 1.6 | 1.4 | 1.0 | 0.9 | 0.9 | ND | ND | ND | ND | ND |
| Sample D | + | + | + | + | + | + | + | + | + | + | + | + |
| | 3.0 | 3.0 | 3.0 | 3.0 | 2.9 | 2.9 | 2.9 | 3.0 | 3.0 | 2.9 | 2.9 | 2.7 |

Chain of reactions of chlorous acid, chlorine dioxide, and acidic chlorite ion

[CHEMICAL FORMULA 4]

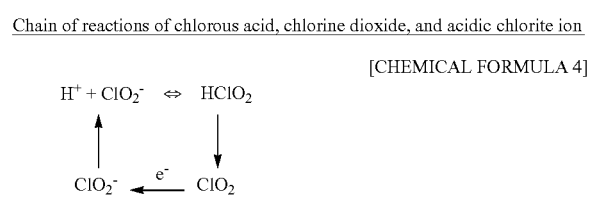

Figure 10:
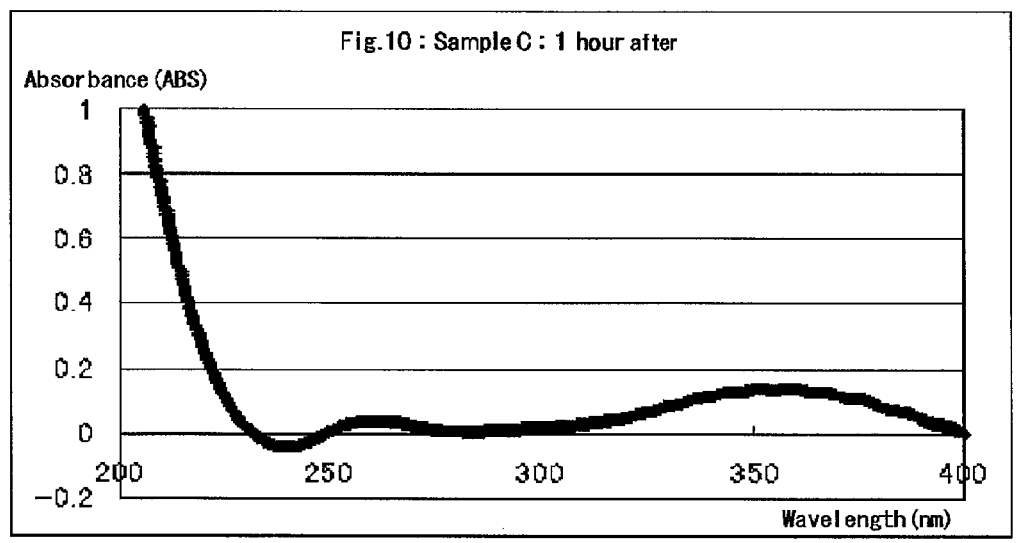
FIG. 10 shows the results of spectrophotometric measurement of sample C conducted on 1 hour of preparation.
Figure 11:
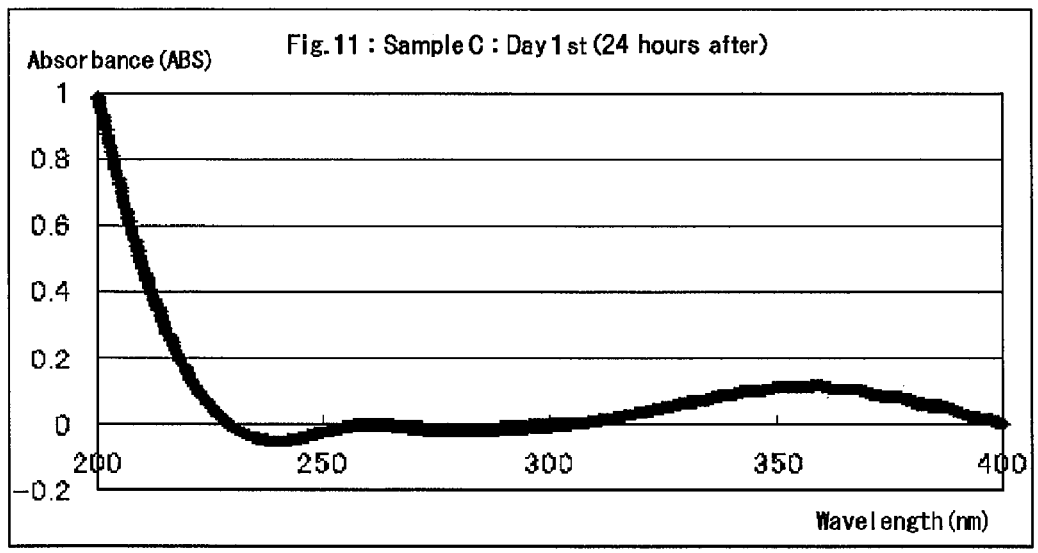
FIG. 11 shows the results of spectrophotometric measurement of sample C conducted on day 1 of preparation.
Figure 12:
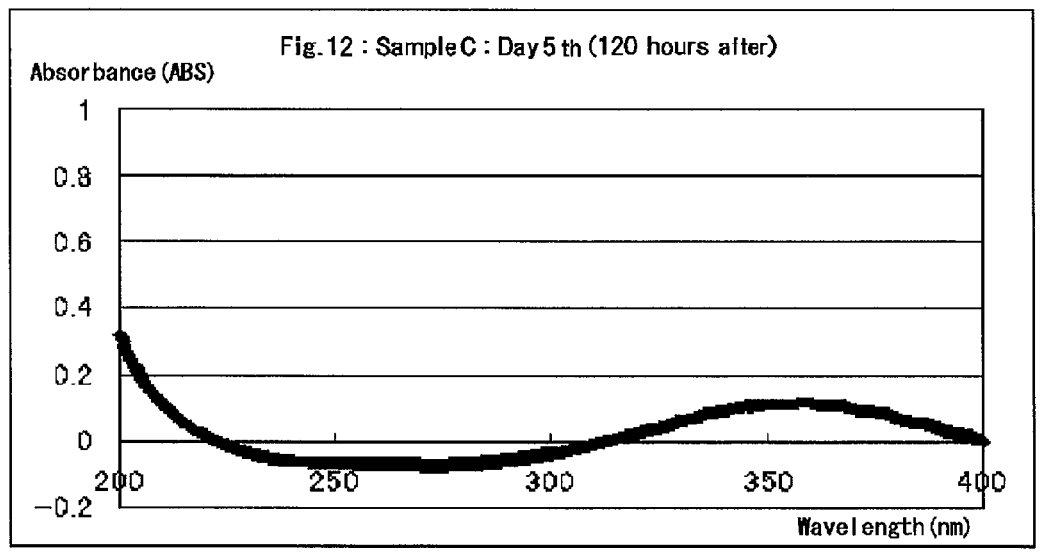
FIG. 12 shows the results of spectrophotometric measurement of sample C conducted on day 5 of preparation.
Figure 13:
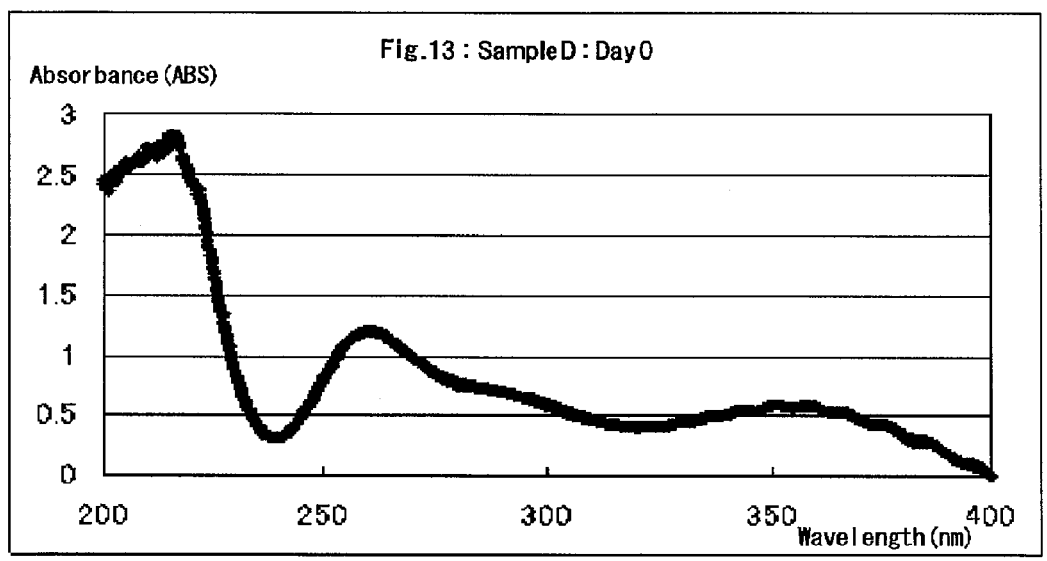
FIG. 13 shows the results of spectrophotometric measurement of sample D conducted on the day of preparation.
Figure 14:
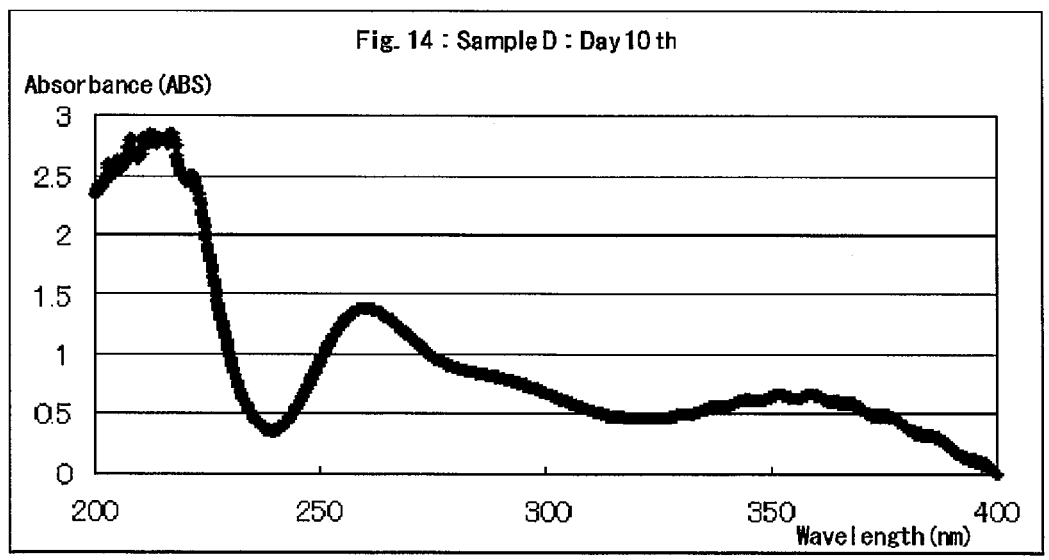
FIG. 14 shows the results of spectrophotometric measurement of sample D conducted on day 10 of preparation.
Figure 15:
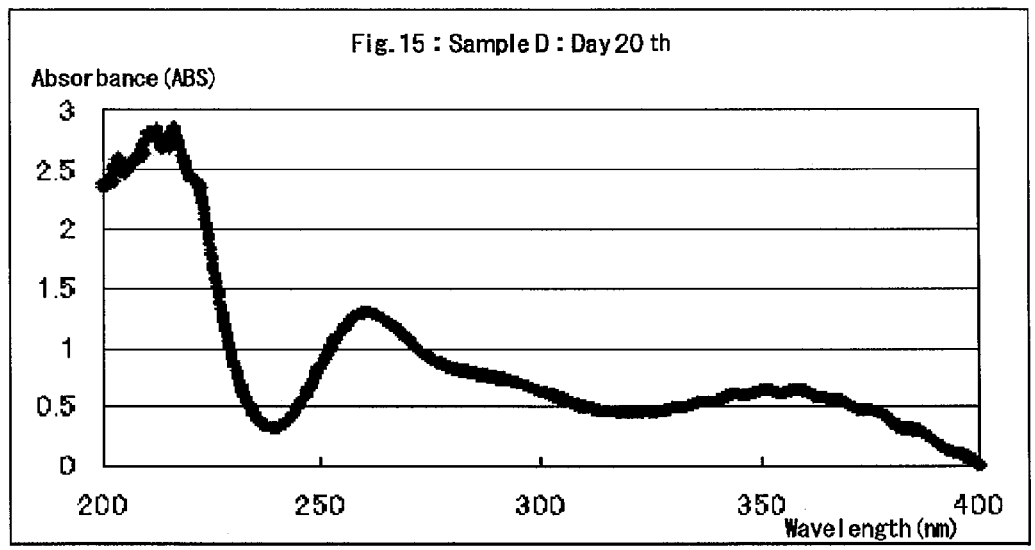
FIG. 15 shows the results of spectrophotometric measurement of sample D conducted on day 20 of preparation.

For sample C, although the presence of two peaks was clearly recognizable at 1 hour (FIG. 10), the two peaks became less visible at 24 hours (FIG. 11), and thereafter the measurement results presented a single peak near 350 nm (FIG. 12). These changes indicate the progress of conversion of chlorous acid to chlorine dioxide.

Figure 4:
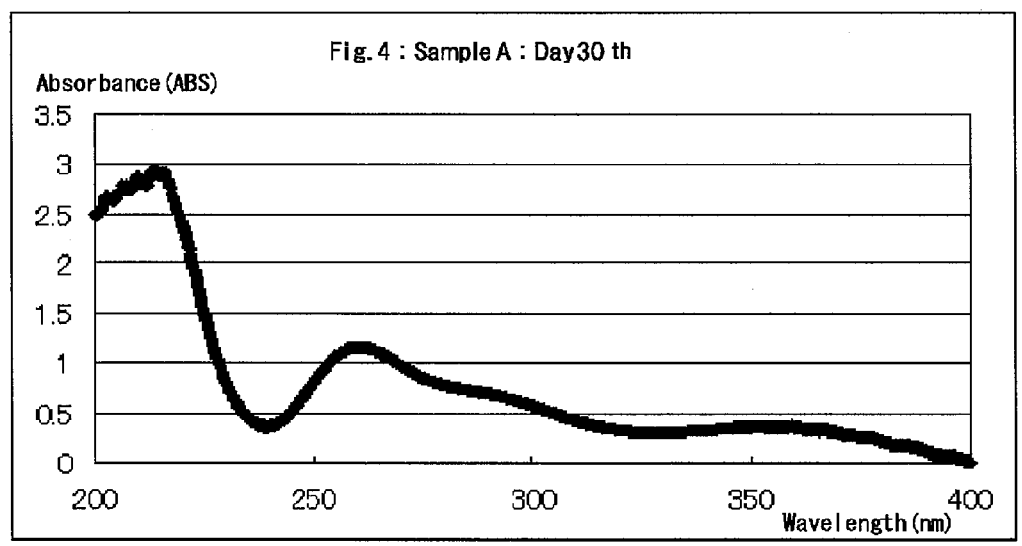
FIG. 4 shows the results of spectrophotometric measurement of sample A conducted on day 30 of preparation.
Figure 5:
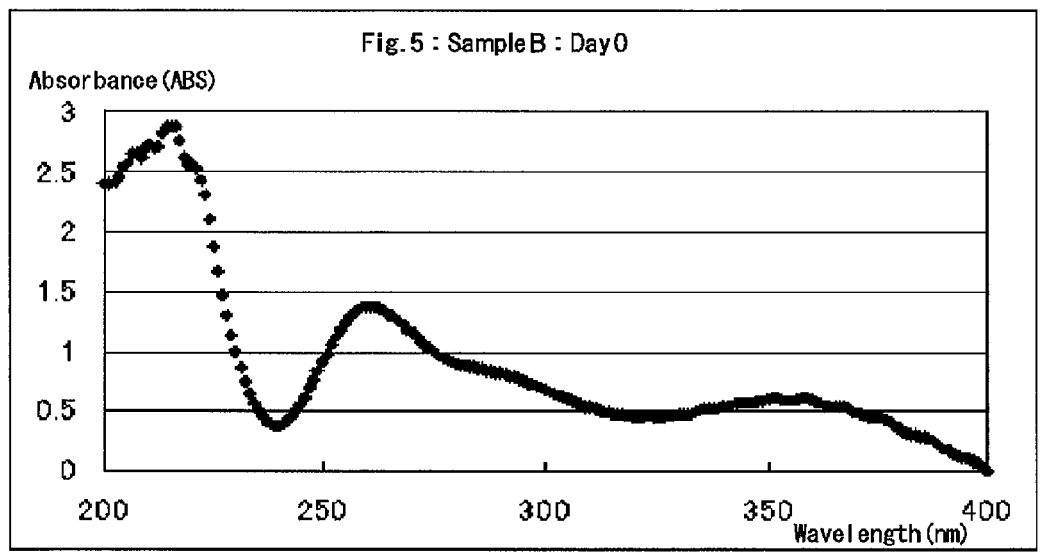
FIG. 5 shows the results of spectrophotometric measurement of sample B conducted on the day of preparation.
Figure 6:
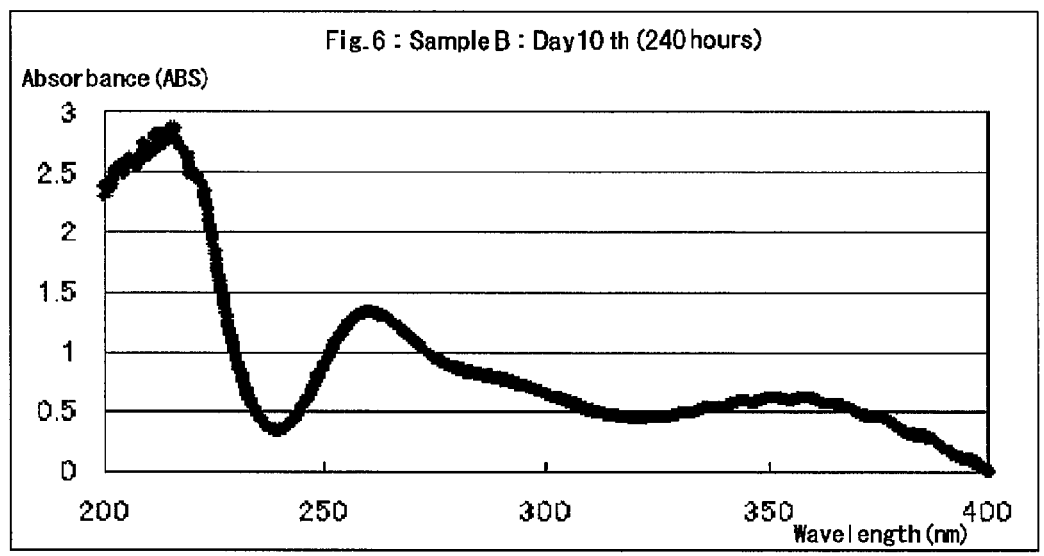
FIG. 6 shows the results of spectrophotometric measurement of sample B conducted on day 10 of preparation.
Figure 7:
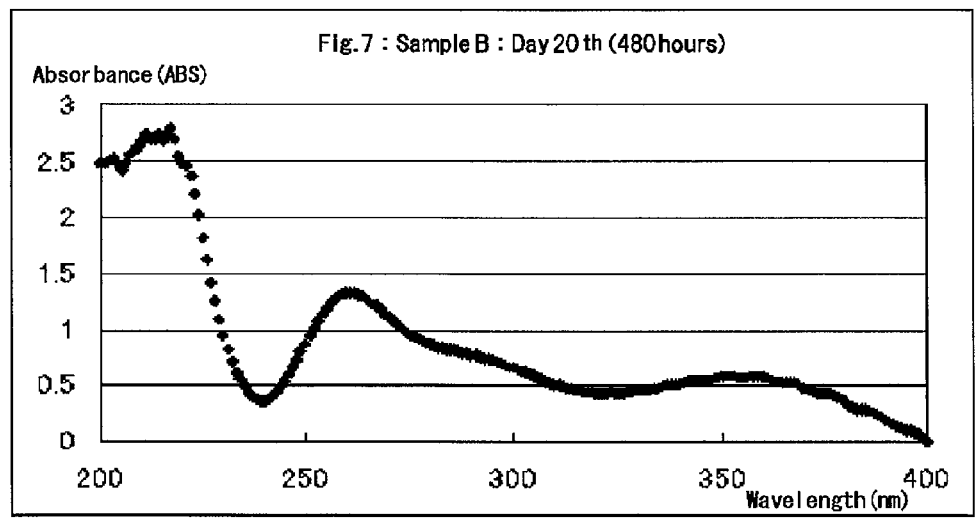
FIG. 7 shows the results of spectrophotometric measurement of sample B conducted on day 20 of preparation.
Figure 8:
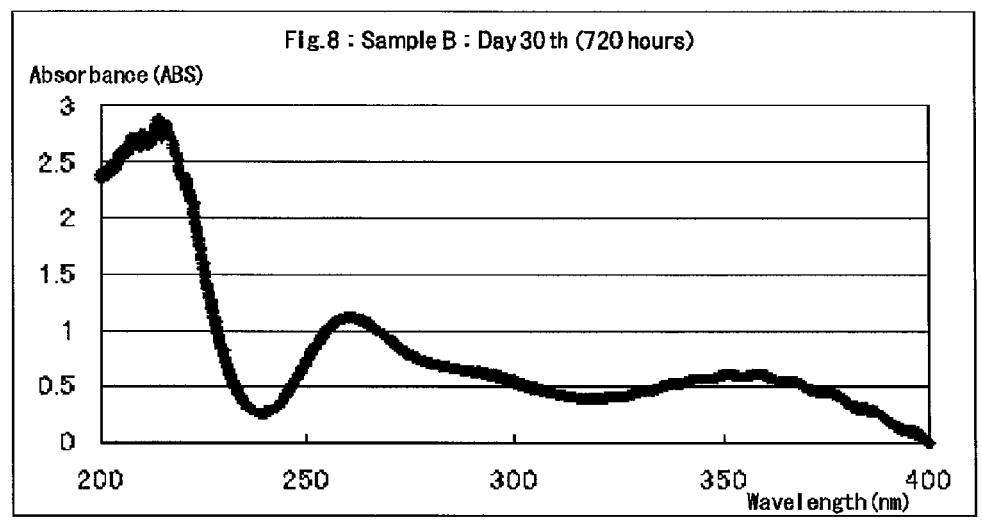
FIG. 8 shows the results of spectrophotometric measurement of sample B conducted on day 30 of preparation.
Figure 9:
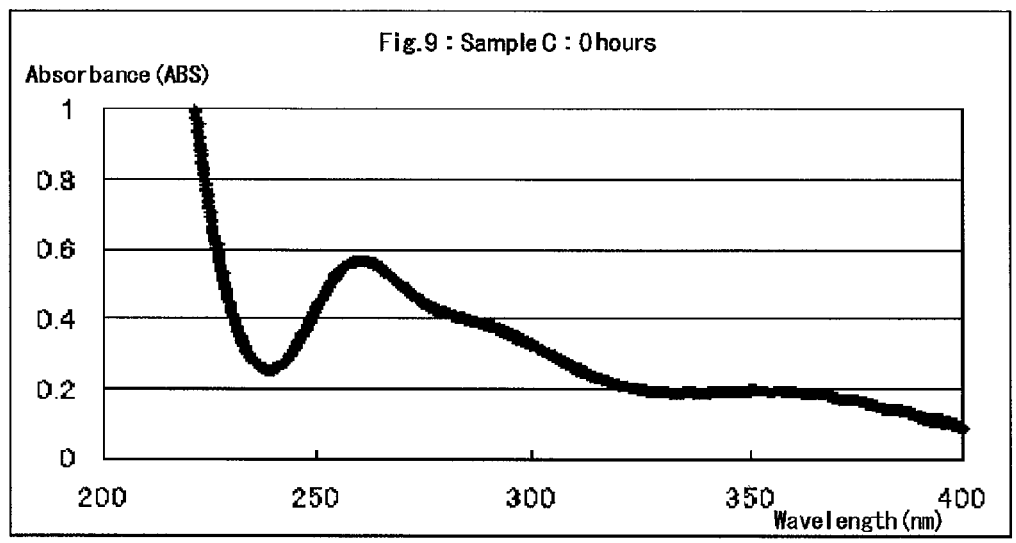
FIG. 9 shows the results of spectrophotometric measurement of sample C conducted on the day of preparation.
Figure 16:
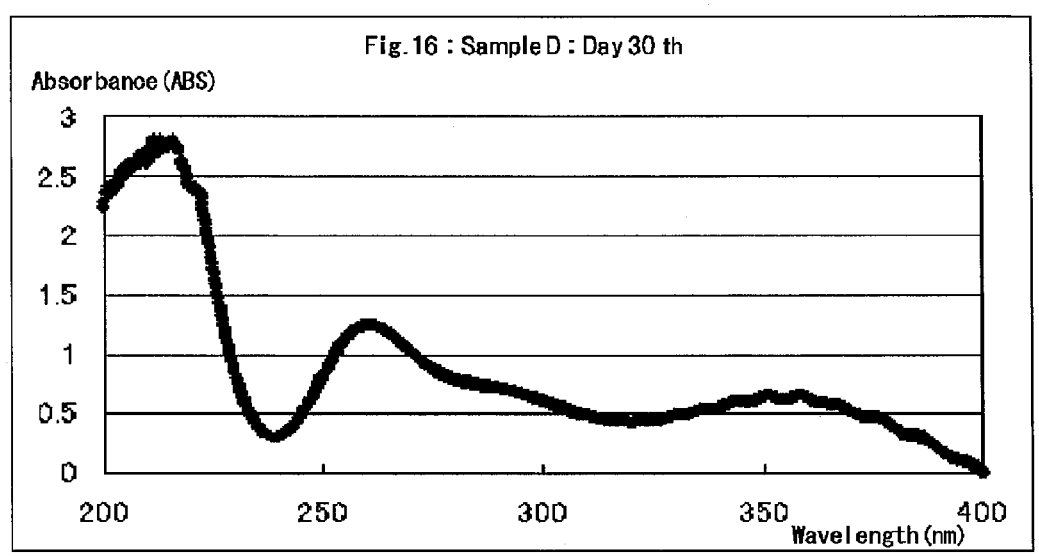
FIG. 16 shows the results of spectrophotometric measurement of sample A conducted on day 30 of preparation.

Meanwhile, samples A, B, and D showed two peaks near 260 and 350 nm after 30 days (FIGS. 4, 8, and 16). It follows that the aqueous chlorous acid solution of the present invention provides more stable chlorous acid solutions than conventional disinfectants.

Of these, sample B, as shown in FIGS. 5, 6, 7, and 8, which illustrate the time course of changes in UV absorption, demonstrates marked changes in the shape of the two peaks as the period extends to 10, 20, and 30 days. On the contrary, samples A and D maintained on day 30 the two peaks observed on day 0 (FIGS. 1, 2, 3, 4, 13, 14, 15, and 16). These results suggest little change over time for samples A and D in the composition of chlorous acid, chlorite ions, chlorine dioxide, and other chlorine oxide compounds. It is apparent, therefore, that Example 2 (involving addition of inorganic salt), Example 3 (involving addition of inorganic salt followed by addition of inorganic acid and salt), and Example 4 (involving addition of organic acid and salt) preserve the initial composition of the solution better than conventional disinfectants.

Lower figures in each cell represent $HClO_2$ content (%), and upper signs designate UV measurement results: +, presence of two absorption peaks identified at 260 and 350 nm; −, presence of a maximum absorption peak identified only in the vicinity of 350 nm.

Figure 17:
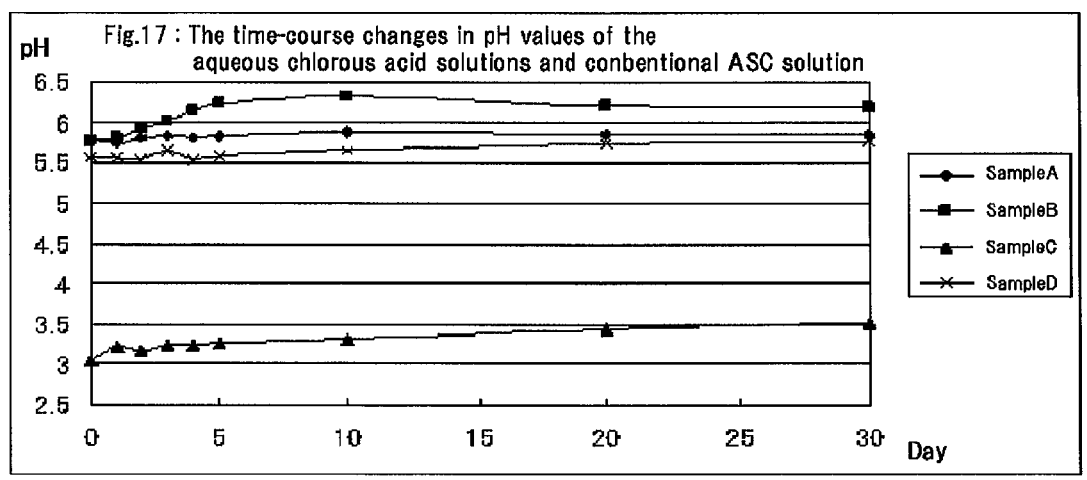
FIG. 17 compares the time-course changes in pH values of the aqueous chlorous acid solutions of Examples 2, 3, and 4 and conventional ASC solution.

FIG. 17 shows the time course of changes in pH values for samples A, B, C, and D. The pH value of sample B, which was initially set at 5.7, temporarily elevated to the order of 6, and gradually decreased thereafter. On the other hand, sample A, which had an initial pH value of 5.8, retained the pH level after 30 days, indicating the effectiveness of the buffering action. Likewise, sample D, which had an initial pH value of 5.7, maintained the pH level after 30 days, indicating the effectiveness of the buffering action. These results indicate that pH can be stabilized either by directly adding a buffer agent to the aqueous solution or by adding a buffer agent after pH adjustment with sodium carbonate.

As can be seen from the above, the aqueous solution obtained by acidifying an aqueous sodium chlorite solution, as in the process for producing ASC, rapidly loses the chlorous acid ($HClO_2$) content by a highly accelerated conversion of the acid to chlorine dioxide ($ClO_2$). The aqueous solutions obtained according to the present invention, however, adjust the shortage or excess of hydrogen ions resulting from oxidation-reduction reactions of chlorine oxides while buffering the pH within a narrow range. Consequently, stabilization of pH contributes to preserving the transitional state of chlorous acid ($HClO_2$): $H^+ + ClO_2^- \rightleftarrows HClO_2$, and this allows for maintaining the chlorous acid content by sustaining the stochiometric balance of molecules and ions in the aqueous chlorous acid solution.

These observations argue that the process of the present invention exhibits superiority in providing an aqueous solution that has a high bactericidal activity and an extended stability of chlorous acid ($HClO_2$).

The present invention achieves a long-term stabilization of chlorous acid, which has a high bactericidal potential. It will, therefore, enable commercial distribution of aqueous chlorous acid solutions on the market that have not been successfully circulated as sales products. It will contribute to widespread social adoption of chlorous acid, which is useful as disinfectant.

So far, the present invention has been explained based on embodiments with reference figures and tables. However, the present invention is not restricted to these implementations, and can be practiced in various modes within the scope of the accompanying claims.

INDUSTRIAL APPLICABILITY

The aqueous chlorous acid solution obtained according to the present invention can be applied for bleaching, removal of bloodstains, and other similar uses, in addition to bactericidal purposes.

The invention claimed is:

1. A process for pretreating food in food-processing operations, comprising the steps of:
   forming a chlorous acid-containing solution using aqueous sodium chlorate solution as a starting material;
   adding to the chlorous acid-containing solution at least one compound selected from the group consisting of inorganic and organic acids and salts or a combination thereof to provide long-term stabilization of said chlorous acid for delaying the conversion of chlorous acid to chlorine dioxide and produce an aqueous solution in a form that is capable of sustaining chlorous acid for an extended time of 30 days, wherein the pH of said aqueous solution is in the range of 3.2 to 7.0; and
   applying the aqueous solution to food as disinfectant for pretreatment of food-processing operations.

2. The process of claim 1, wherein the aqueous solution is formed by adding to the chlorous acid-containing solution at least one compound selected from the group consisting of organic acids and salts or a combination thereof.

3. The process of claim 1, wherein the aqueous solution is formed by adding to the chlorous acid-containing solution at least one compound selected from the group consisting of inorganic acids and salts or a combination thereof.

4. The process of claim 1, wherein said organic acids include succinic acid, citric acid, malic acid, acetic acid, or lactic acid.

5. The process of claim 1, wherein said organic salts include sodium succinate, potassium succinate, sodium citrate, potassium citrate, sodium malate, potassium malate, sodium acetate, potassium acetate, sodium lactate, potassium lactate, or calcium lactate.

6. The process of claim 1, wherein said inorganic acids include carbonic acid, phosphoric acid, boric acid, or sulfuric acid.

7. The process of claim 1, wherein said inorganic salts include carbonates, hydroxides, phosphates, or borates.

8. The process of claim 7, wherein said carbonates include sodium carbonate, potassium carbonate, sodium bicarbonate, or potassium bicarbonate.

9. The process of claim 7, wherein said hydroxides include sodium hydroxide or potassium hydroxide.

10. The process of claim 7, wherein said phosphates include disodium hydrogenphosphate, sodium dihydrogenphosphate, trisodium phosphate, tripotassium phosphate, dipotassium hydrogenphosphate, or potassium dihydrogenphosphate.

11. The process of claim 7, wherein said borates include sodium borate or potassium borate.

12. The process of claim 1, wherein in the aqueous solution, a chain of reaction represented by:

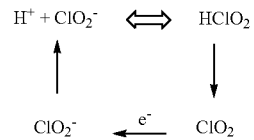

is ongoing.

13. The process of claim 1, wherein the process further comprises providing the chlorous acid-containing solution as a first solution, and the adding comprises adding a second solution comprising the at least one compound selected from the group consisting of inorganic and organic acids and salts or a combination thereof to the first solution.

* * * * *